United States Patent [19]

Gough et al.

[11] 4,035,403

[45] July 12, 1977

[54] ORGANOTIN BORATES

[75] Inventors: Robert George Gough, Fairfield; Francis Joseph Buescher, Cincinnati, both of Ohio

[73] Assignee: Cincinnati Milacron, Inc., Cincinnati, Ohio

[21] Appl. No.: 691,315

[22] Filed: June 1, 1976

[51] Int. Cl.$^2$ .................................... C07F 7/22
[52] U.S. Cl. ........................ 260/429.7; 424/185
[58] Field of Search ................ 260/429.7; 424/185

[56] References Cited

U.S. PATENT DOCUMENTS

| | | | |
|---|---|---|---|
| 2,867,641 | 1/1969 | Ramsden | 260/429.7 |
| 3,312,725 | 4/1967 | Weissenberger | 260/429.7 |
| 3,928,285 | 12/1975 | Gough et al. | 260/45.75 K |

FOREIGN PATENT DOCUMENTS

| | | |
|---|---|---|
| 772,646 | 7/1954 | United Kingdom |

OTHER PUBLICATIONS

Mehrotra et al., J. of Organometallic Chemistry, 47, pp. 39–44 (1973).
Mehrotra et al., J. of Organometallic Chemistry, V65, pp. 361 to 366 and 367–376.

*Primary Examiner*—Helen M. S. Sneed
*Attorney, Agent, or Firm*—D Dunn

[57] ABSTRACT

Novel organotin borates having a tin-halogen bond are provided the phase which are useful as bacteriocides.

25 Claims, No Drawings

ORGANOTIN BORATES

BACKGROUND OF THE INVENTION

This invention relates to novel compositions of matter which are organotin borates having a tin-halogen bond. The novel tin-halogen bond containing organotin borates of this invention have been found to exhibit fungicidal activity.

Various organotin borates have been known in the art for some time and their diverse use as fungicides, anti-microbial agents, anti-oxidants and polymer stabilizers have been reported. Organotin borates of the general formula $(R_2Sn)_{3-n}R^1(BO_3)_2$ (I) where R and $R^1$ are alkyl, aryl or aralkyl radicals and n is 0, 1 or 2 are disclosed by H. E. Ramsden in U.S. Pat. No. 2,867,641 as stabilizers for chlorine containing resins. G. Weissenberger, in U.S. Pat. No. 3,312,725 disclosed organotin borates having the formula $[R^1, R^2, R^3Sn\,O]_a B(OH)_{3-a}$ (II) where $R_1$, $R_2$ and $R_3$ are aliphatic, araliphatic, cycloaliphatic or aromatic radicals and a is 1 to 3 and their use as biological toxicants. Organotin borates having the general formula $[R_1, R_2, R_3 SnO]_{3-x}B-(OH)_x$ (III) where $R_1$, $R_2$ and $R_3$ are alkyl radicals and x is 0 or 1 are disclosed in West German Auslegeschrift No. 1,246,732. S. K. Mehrotra et al in the Journal of Organometallic Chemistry Vol. 65 at pages 361 to 366 and pages 367 to 376 (1974) disclosed organotin borates having the formulae

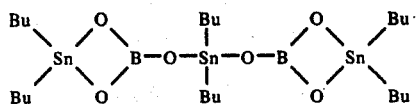 (IV),

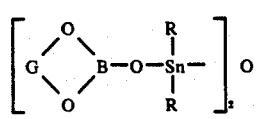 (V)

where R is methyl or butyl and G is $CMe_2CH_2CH-Me-$, $-CMe_2-CMe_2-$ or $-CHMe-CH_2-$,

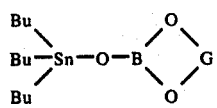 (VI)

where G is defined as in formula V,

 (VII)

where R is Me, Et, Pr, Bu, Bu-i, Ph,

 (VIII)

where R is Et, Pr, Bu and Bu-i, and

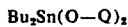 (IX)

where Q is

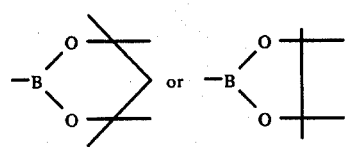

Organotin borate compounds having the formulae

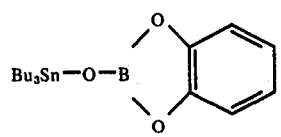 (X)

and

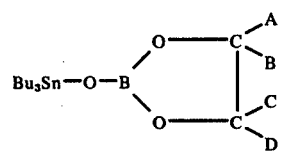 (XI)

where
A,B,C,D = H
A,B,C, = H; D = Me
A,B,C,D = Me and

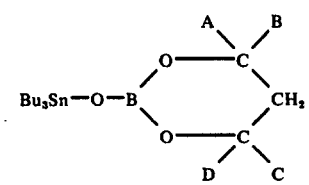 (XII)

where
A,B,C,D = H
A,B,C = Me; D = H are disclosed by S. K. Mehrotra et al. in the Journal of Organometallic Chemistry, Vol. 47 pages 39 to 44 (1973).

SUMMARY OF THE INVENTION

The organotin borate compounds of this invention may be described by the following general formula

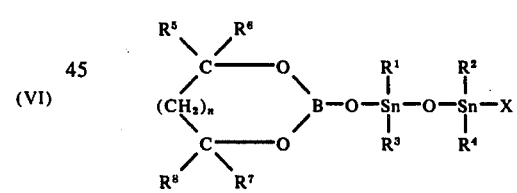

where:
$R^1$, $R^2$, $R^3$ and $R^4$ are the same or different and are aryl, aralkyl, alkaryl or $C_1$ to $C_8$ alkyl groups;
$R^5$ and $R^7$ are hydrogen or $C_1$ to $C_4$ alkyl group;
$R^6$ and $R^8$ are $C_1$ to $C_4$ alkyl group;
X is chlorine or bromine; and
n is 0, 1 or 2.

In contrast to many organotin borates known in the art the organotin borates of this invention have surprisingly been found to be highly stable and exhibit good resistance to hydrolysis.

DESCRIPTION OF THE INVENTION

In accordance with this invention there are provided organotin borate compounds represented by the following general formula

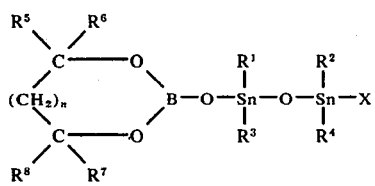

where:

R¹, R², R³ and R⁴ are the same or different and are aryl, aralkyl, alkaryl or $C_1$ to $C_8$ alkyl groups;

R⁵ and R⁷ are hydrogen or $C_1$ to $C_4$ alkyl group;

R⁶ and R⁸ are $C_1$ to $C_4$ alkyl group;

X is chlorine or bromine and n is 0, 1 or 2

Where any or all of R¹, R², R³ and R⁴ are aryl they may for example include phenyl.

When any or all of R¹, R², R³ and R⁴ are aralkyl groups such groups could include, but are not limited to, benzyl, phenethyl and phenpropyl.

In the case where any or all of R¹, R², R³ and R⁴ are alkaryl groups such groups are to be defined by the formula

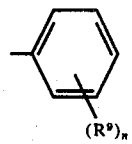

where R⁹ is a $C_1$ to $C_4$ alkyl group, examples of which are methyl, ethyl propyl, isopropyl, butyl, isobutyl and tertiary butyl groups, and n is 1, 2 or 3. Thus, the alkaryl group include, but are not limited to o-toyl, m-tolyl, p-tolyl, 2,3-xylyl, 2,4-xylyl, 3,5-xylyl, 2,6-xylyl, mesityl, m-cumenyl, p-cumenyl, O-butyl phenyl, m-butyl phenyl, p-butyl phenyl, 2,3-di butyl phenyl, 2,4-di butyl phenyl, 3,5-dibutyl phenyl, 2,6-dibutyl phenyl, p-ethyl phenyl, 3,5-diethyl phenyl, 2,4-diethyl phenyl, m-propyl phenyl, p-propyl phenyl, 2,4-dipropyl phenyl, 3,5-dipropyl phenyl, 2,6-dipropyl phenyl, p-isopropyl phenyl, 3,5-diisopropyl phenyl, m-isobutyl phenyl, 3,5-diisobutyl phenyl, p-tertiarybutyl phenyl, 3,5-ditertiarybutyl phenyl, 2,4,6-triethylphenyl, 2,4,6-tripropyl phenyl and 2,4,6-tributyl phenyl.

In the organotin borate compounds of this invention where any or all of R¹, R², R³ and R⁴ are $C_1$ to $C_8$ alkyl groups such groups include, but are not limited to methyl, ethyl, propyl, butyl, pentyl, hexyl, octyl, isopropyl, isobutyl, tertiary butyl, 2-ethylhexyl and isooctyl.

Wherein R⁵, R₆, R⁷ and R⁸ are $C_1$ to $C_4$ alkyl groups examples of such groups include methyl, ethyl, propyl, isopropyl, butyl, isobutyl and tertiary butyl groups.

As examples of organotin borate compounds within the scope of this invention there include but not limited to, the following compounds by reference to the following formula.

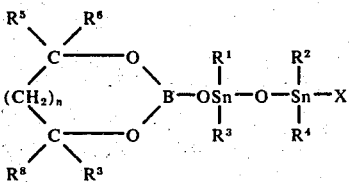

Where

| R¹ | R² | R³ | R⁴ | R⁵ | R⁶ | R⁷ | R⁸ | X | n |
|---|---|---|---|---|---|---|---|---|---|
| Me | Me | Me | Me | H | Me | H | Me | Cl | 0 |
| Me | Me | Me | Me | Me | Me | Me | Me | Br | 0 |
| Me | Me | Me | Me | Me | Me | Me | Me | Cl | 1 |
| Bu | Bu | Bu | Bu | H | Me | H | Me | Cl | 1 |
| Bu | Bu | Bu | Bu | H | Me | H | Me | Br | 0 |
| Et | Et | Et | Et | H | Me | H | Me | Cl | 1 |
| Pr | Pr | Pr | Pr | Me | Me | Me | Me | Br | 2 |
| Hex | Hex | Hex | Hex | H | Me | H | Me | Cl | 0 |
| Oct | Oct | Oct | Oct | Me | Me | Me | Me | Br | 1 |
| Me | Me | Me | Me | H | Bu | H | Bu | Cl | 0 |
| Me | Me | Me | Me | H | Et | H | Et | Br | 1 |
| Me | Me | Me | Me | H | Me | Me | Me | Cl | 1 |
| Ph | Ph | Ph | Ph | H | Me | H | Me | Cl | 1 |
| Bz | Bz | Bz | Bz | H | Me | H | Me | Cl | 0 |
| PhE | PhE | PhE | PhE | H | Me | H | Me | Br | 1 |
| PhP | PhP | PhP | PhP | H | Me | H | Me | Cl | 1 |
| p-Tol | p-Tol | p-Tol | p-Tol | H | Me | H | Me | Cl | 0 |
| 2,4-Xy | 2,4-Xy | 2,4-Xy | 2,4-Xy | H | Me | H | Me | Br | 0 |
| p-Cum | p-Cum | p-Cum | p-Cum | H | Me | H | Me | Cl | 1 |
| p-BuPh | p-BuPh | p-BuPh | p-BuPh | H | Me | H | Me | Cl | 0 |
| Me | Bu | Me | Bu | H | Me | H | Me | Cl | 1 |
| Me | Oct | Me | Oct | H | Me | H | Me | Br | 1 |
| Me | Ph | Me | Ph | H | Me | H | Me | Cl | 1 |
| Ph | Bz | Ph | Bz | H | Me | H | Me | Cl | 0 |
| Me | PhE | Me | PhE | H | Me | H | Me | Br | 1 |
| PhE | p-Tol | PhE | p-Tol | H | Me | H | Me | Cl | 1 |

As used above in the exemplary compounds Me = methyl, Et = ethyl, Pr = propyl, Bu = butyl, Hex = hexyl, Oct = octyl, Ph = phenyl, Bz = benzyl, PhE = phenethyl, PhP = phenpropyl, p-Tol = p-tolyl, 2,4-Xy = 2,4 xylyl, p-Cum = p-cumenyl and p-BuPh = p-butyl-phenyl radicals.

The organotin borates of this invention have been found to exhibit anti microbial activity with respect to bacteria such as Pseudomona sp, Alcaligenes sp, Achromobacter sp and Acinetobacter sp and mold such as Fusarium sp, Penicillium sp and Cephalosporium sp. Weissenberger, U.S. Pat. No. 3,312,725 has disclosed organotin borates having the formula $(R^1, R^2, R^3SnO)_a B(OH)_{3-a}$ where R¹, R² and R³ are identical or, different aliphatic, araliphatic, cycloaliphatic or aromatic radicals and a is a whole number from 1 to 3 as useful for combatting pests such as bacteria, amoebas, nematodes, larvae, insects and fungi and such disclosure is incorporated herein by reference.

Various embodiments of this invention may be practiced in accordance with the following general formula

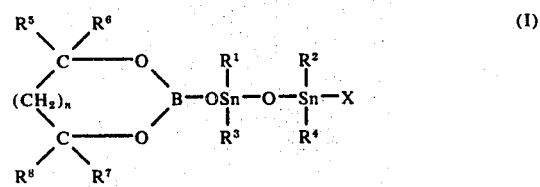

where R¹, R², R³, R⁴, R⁵, R⁶, R⁷, R⁸, X and n are as previously defined herein with respect to the above general formula. Among some of the preferred embodiments of this invention are those compounds, in accordance with the above general formula, wherein (I-a) R¹, R², R³, R⁴, R⁵, R⁶ and R⁸ are methyl, R⁷ is hydrogen X is chlorine, and n is 1; (I-b) R¹, R², R³ and R⁴ are butyl, R⁵ is hydrogen, R⁶, R⁷ and R⁸ are methyl, X is chlorine and n is 1; (I-c) R¹, R², R³ and R⁴ are butyl, R⁶, R⁷ and R⁸ are methyl, R⁵ is hydrogen, X is bromine and n is 1; (I-d) R¹, R², R³, R⁴, R⁶, R⁷ and R⁸ are methyl, R⁵ is hydrogen, X is bromine and n is 1; and (I-e) R¹, R², R³ and R⁴ are octyl, R⁶, R⁷ and R⁸ are methyl, R⁵ is hydrogen, X is chlorine and $n$ is 1.

A number of methods may be used to prepare the organotin borates of this invention. One method is to react a borate ester of a glycol with a 1-halo-3-hydroxy-1,1,3,3-tetraalkyldistannoxane in a solvent forming an azeotrope with water, with removal of water by azeotropic distillation. In another method a borate ester of a glycol may be reacted with a 1-halo-3-hydroxy-1,1,3,3-tetraalkyldistannoxane in the absence of solvent.

In the method of preparation of the organotin borates of this invention wherein a borate ester of a glycol is employed the borate ester may be prepared by reacting boric acid or boric anhydride with a glycol. The preparation of borate esters of glycols has been described by C. H. Steinberg and D. L. Hunter in Industrial and Engineering Chemistry, Vol, 49, pages 174–181 (1957), the disclosure of which is incorporated herein by reference. Suitable glycols include, but are not limited to, 2-methyl-2,4-pentanediol; 2,4-dimethyl-2,4-pentanediol; 2,3-dimethyl-2,3-butanediol and 2,5-dimethyl-2,5-hexanediol.

As typical halogen containing distannoxanes usable in the preparation of the organotin borates of this invention there include, but not limited to, 1-chloro-3-hydroxy-1,1,3,3-tetramethyldistannoxane; 1-bromo-3-hydroxy-1,1,3,3-tetramethyl distannoxane; 1-chloro-3-hydroxy-1,1,3,3-tetrabutyldistannoxane; 1-bromo-3-hydroxy-1,1,3,3-tetrabutyldistannoxane; 1-chloro-3-hydroxy-1,1,3,3-tetraoctyldistannoxane; 1-chloro-3-hydroxy-1,1,3,3-tetraphenyl distannoxane; 1-bromo-3-hydroxy-1,1,3,3-tetrabenzyl distannoxane; 1-bromo-3-hydroxy-1,1,3,3-tetra p-tolyl distannoxane; 1-chloro-3-hydroxy-1,1,3,3-tetra p-cumenyl distannoxane; 1-chloro-3-hydroxy-1,1,3,3-tetra (p-butyl phenyl)distannoxane; 1-bromo-3-hydroxy-1,1,3,3-tetra(3,5-diethylphenyl) distannoxane; 1-chloro-3-hydroxy-1,1,3,3-tetra(3,5 diisopropyl phenyl) distannoxane and 1-bromo-3-hydroxy-1,1,3,3-tetra(2,4,6-tributylphenyl) distannoxane. The halogen containing distannoxanes used in the preparation of the organotin compounds of this invention can be prepared by such methods as are disclosed by R. Okawara and M. Wada in the Journal of Organometallic Chemistry, Vol. 1, pages 81–88 (1963) and A. G. Davies, L. Smith, P. J. Smith and W. McFarlane in the Journal of Organometallic Chemistry, Vol. 29, page 245 (1971), which disclosures are incorporated herein by reference.

This invention will be further described by the following nonlimiting examples, in which all temperatures are in °C and all percentages are by weight unless otherwise indicated.

EXAMPLE 1

Preparation of 4,4,6-trimethyl-2-hydroxy-1,3,2-dioxaborinane.

Boric acid (1 mole) and 2-methyl-2,4-pentanediol (1 mole) were placed in a reaction vessel with 1000 ml of benzene and the mixture refluxed until 2 moles of water were removed. Evaporation of the benzene at reduced pressure gave a liquid which slowly crystallized to give a white solid mp 73°–75° C [literature mp 69°–70° C, H. Steinberg and D. L. Hunter, Ind. & Eng. Chem 49°, 174°–181 (1957)].

EXAMPLE 2

Preparation of 1-(4,4,6-trimethyl-1,3,2-dioxaborinyl-2-oxy)-3-chloro-1,1,3,3-tetramethyldistannoxane (I-a)

The title compound was prepared by reacting 0.0273 mole, 10.00 gms, of 1-hydroxy-3-chloro-1,1,3,3-tetramethyl-distannoxane with 0.0273 mole, 3.93 gm, of 4,4,6-trimethyl-2-hydroxy-1,3,2-dioxaborinane. The reaction was carried out in refluxing benzene with the water byproduct being removed as the azeotrope. After 1.5 hrs. refluxing, a 100% yield of water was obtained. Evaporation of the solvent gave a quantitative yield of crude product with mp 253°–255° C. Crystallization from acetonitrile gave a 43% yield of white crystals, mp 252°–253° C. Elemental analysis: found (calculated): C 24.27% (24.42%), H 4.76% (4.92%), B 1.70% (2.20%), Sn 47.65% (48.25%), Cl 7.12% (7.21%). The 1-hydroxy-3-chloro-1,1,3,3-tetramethyldistannoxane was prepared by the method of Okawara [R. Okawara and M. Wada, J. Organometal. Chem. 1, 81–88(1963)].

The compound showed a mass spectrograph with a parent ion molecular weight of 492 (calculated: 492), and peak patterns at mass 185

$[(CH_3)_2Sn - Cl]$, mass 309

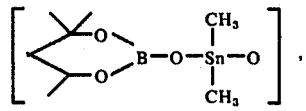

mass 165 $[(CH_3)_2SnO\ ]$ and mass 128

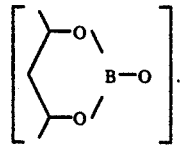

The patterns showed excellent agreement with the patterns calculated on the basis of isotope abundances of Sn, B, and Cl.

EXAMPLE 3

Preparation of 1-(4,4,6-trimethyl-1,3,2-dioxaborinyl-2-oxy)-3-chloro-1,1,3,3-tetrabutyldistannoxane (I-b)

The product was obtained by the reaction of 0.022 mole of 1-chloro-3-hydroxy-1,1,3,3-tetrabutyldistannoxane with 0.022 mole of 4,4,6-trimethyl-2-hydroxy-1,3,2-dioxaborinane. The reaction was carried out in reluxing benzene with the water byproduct being removed as the azeotrope. After 15.5 hours of refluxing, a 75% of the theoretical amount of water had been collected. Evaporation of the benzene gave a product which crystallized to an off-white, waxy material, mp 75°–79° C. The infrared spectrum (neat, NaCl) showed bands at 3100(w), 3080(w), 3045(m), 2930(m), 2870(m), 1960(w), 1820(w), 1485(m), 1465(m), 1420(m), 1380(s), 1355(s), 1300(s), 1270(m), 1230(m), 1210(m), 1170(m), 1080(w), 1040(w), 870(w), 820(w), 770(w), 680(s), 580(s), cm$^{-1}$. Presence of halogen was verified by a sodium fusion test. (a) R. Okawara and M. Wada, J. Organometal. Chem., 1, 81-88(1963).

EXAMPLE 4
Preparation of 1-(4,4,6-trimethyl-1,3,2-dioxaborinyl-2-oxy)-3-bromo-1,1,3,3-tetrabutyldistannoxane (I-c)

The product was obtained by the reaction of 0.022 mole of 1-bromo-3-hydroxy-1,1,3,3-tetrabutyldistannoxane with 0.022 mole of 4,4,6-trimethyl-2-hydroxy-1,3,2-dioxaborinane. A benzene solution of the reagents was refluxed until no more water was being removed as the azeotrope. Evaporation of the benzene at reduced pressure gave a product which formed waxy crystals, mp 54°-56° C, in near quantitative yield. The infrared spectrum (melt on NaCl plates) showed bands at 2970(s), 2940(s), 2890(s), 2870(s), 1466(s), 1420(s), 1380(s), 1355(s), 1300(s), 1275(s), 1227(m), 1210(s), 1170(s) 1080(m), 875(m), 820(m), 770(m), and 675(s), cm$^{-1}$.

Elemental analysis: found (calculated): carbon, 37.22% (37.49%); hydrogen, 7.08% (6.87%); bromine, 11.33% (11.34%). (a) R. Okaware and M. Wada, J. Organometal, Chem., 1, 81-88(1963).

EXAMPLE 5
Fungicidal Activity Test of 1-(4,4,6-trimethyl-1,3,2 dioxaborinyl-2-oxy)-3-chloro-1,1,3,3-tetramethyl distannoxane Test Fluid

| | |
|---|---|
| Oleic acid | 0.5 parts by weight |
| Triethanol amine | 0.5 parts by weight |
| Water* | 99.0 parts by weight |

*Sterile distilled water

Procedure 100 ml units of the aqueous test fluid were placed in separate sterile 150 ml beakers and one of the units (i.e. control unit) innoculated with 1 ml of a standard mixture of Fusarium sp, Penicillium sp and Cephalosporium sp mold cultures. To another of the 100 ml units there was added 2500 ppm (parts per million) of the additive (i.e., 1-(4,4,6-trimethyl-1,3,2-dioxaborinyl-2-oxy) -3-chloro-1,1,3,3-tetramethyldistannoxane). A mold total plate count sample was withdrawn from the control unit, the mold count determined, the beakers then covered with perforated aluminum foil and then the beakers placed on a shaker. Three hours later a mold total plate count sample was taken from the control unit and the mold count determined. Subsequent mold total plate count samples were taken and mold count determinations made at the time intervals indicated in Table I. At 72 hours after the start of the test program the control unit of test fluid was reinnoculated with 1 ml of the mold mixture, after withdrawal of the mold total plate count samples and the unit containing the additive was innoculated with 2 ml of the mold mixture. 168 hours after the starting of the test program mold total plate count samples were withdrawn from the test fluid units, mold count determinations made and then to the unit of test fluid containing the additive there was added another 2500 parts per million (ppm) of the additive (i.e., organotin borate compound). At 312 hours after the start of the test program and after removing the mold total plate count sample an additional 2500 ppm of the additive were added to the unit of test fluid already containing the additive. The test program was then continued as shown in Table I.

TABLE I

| Time in. Hours | Concentration of the Additive* (ppm) | Mold Titer of Test Fluid with Additive | Mold Titer*** of Control** |
|---|---|---|---|
| 0 | 2500 | — | 2500 |
| 3 | 2500 | — | 2700 |
| 24 | 2500 | — | 4200 |
| 48 | 2500 | — | 2500 |
| 72 | 2500 | — | 2600 |
| 168 | 5000 | 13,800 | 16,200 |
| 171 | 5000 | 16,500 | 15,400 |
| 192 | 5000 | 13,000 | 11,600 |
| 216 | 5000 | 3,800 | 4,000 |
| 240 | 5000 | 6,200 | 6,800 |
| 312 | 7500 | 100 | 2,200 |
| 336 | 7500 | 900 | 3,400 |
| 340 | 7500 | 400 | 3,600 |
| 360 | 7500 | 300 | 1,660,000 |

*Concentration of 1-(4,4,6-trimethyl-1,3,2-dioxaborinyl 2-oxy)-3-chloro-1,1,3,3-tetramethyl distannoxane in the test fluid.
**Test fluid without the additive
***Mold count per ml of test fluid

What is claimed is:

1. A compound having the following general formula

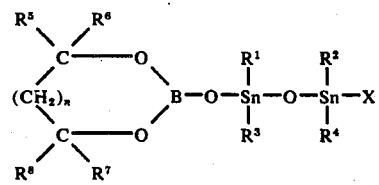

wherein:
R$^1$, R$^2$, R$^3$ and R$^4$ are the same or different and are selected from the group consisting of aryl, aralkyl, alkaryl or C$_1$ to C$_8$ alkyl groups,
R$^5$ and R$^7$ are hydrogen or C$_1$ to C$_4$ alkyl groups,
R$^6$ and R$^8$ are C$_1$ to C$_4$ alkyl groups,
X is chlorine or bromine and
$n$ is 0, 1 or 2.

2. The compounds of claim 1, wherein X is chlorine.
3. The compound of claim 1, wherein X is bromine.
4. The compound of claim 2 wherein $n$ is 0.
5. The compound of claim 2 wherein $n$ is 1.
6. The compound of claim 3 wherein $n$ is 0.
7. The compound of claim 3 wherein $n$ is 1.
8. The compound of claim 1, wherein R$^1$, R$^2$, R$^3$ and R$^4$ and C$_1$ to C$_8$ alkyl groups.
9. The compound of claim 8 wherein R$^5$ is hydrogen and R$^6$, R$^7$ and R$^8$ are C$_1$ to C$_4$ alkyl groups.
10. The compound of claim 8, wherein R$^5$, R$^6$, R$^7$ and R$^8$ are C$_1$ to C$_4$ alkyl groups.
11. The compound of claim 9, wherein X is chlorine.
12. The compound of claim 9, wherein X is bromine.
13. The compound of claim 10, wherein X is chlorine.
14. The compound of claim 10, wherein X is bromine.
15. The compound of claim 11, wherein $n$ is 0.
16. The compound of claim 11, wherein $n$ is 1.
17. The compound of claim 12, wherein $n = 0$.
18. The compound of claim 12, wherein $n = 1$.

19. The compound of claim 1, wherein $R^1$, $R^2$, $R^3$ and $R^4$ are aryl groups.

20. The compound of claim 1, wherein $R^1$, $R^2$, $R^3$ and $R^4$ are aralkyl groups.

21. The compound of claim 1, wherein $R^1$, $R^2$, $R^3$ and $R^4$ are alkaryl groups.

22. The compound of claim 1, wherein $R^1$ and $R^3$ are $C_1$ to $C_8$ alkyl groups and $R^2$ and $R^4$ are aryl groups.

23. The compound of claim 1, which is 1-(4,4,6-trimethyl-1,3,2-dioxaborinyl-2-oxy)-3-chloro-1,1,3,3-tetramethyldistannoxane.

24. The compound of claim 1, which is 1-(4,4,6-trimethyl-1,3,2-dioxaborinyl-2-oxy)-3-chloro-1,1,3,3-tetrabutyldistannoxane.

25. The compound of claim 1, which is 1-(4,4,6-trimethyl-1,3,2-dioxaborinyl-2-oxy)-3-bromo-1,1,3,3-tetrabutyldistannoxane.

* * * * *